United States Patent [19]
Charbonnier et al.

[11] Patent Number: 5,668,622
[45] Date of Patent: Sep. 16, 1997

[54] DEVICE FOR MEASURING THE POSITION OF THE FIXING POINT OF AN EYE ON A TARGET, METHOD FOR ILLUMINATING THE EYE AND APPLICATION FOR DISPLAYING IMAGES WHICH CHANGE ACCORDING TO THE MOVEMENTS OF THE EYE

[75] Inventors: Colette Charbonnier, Pont de Claix; Dominique Masse, Coublevie, both of France

[73] Assignee: Commissariat A L'Energie Atomique, Paris, France

[21] Appl. No.: 616,888

[22] Filed: Mar. 18, 1996

[30] Foreign Application Priority Data

Mar. 24, 1995 [FR] France ................... 95 00489

[51] Int. Cl.$^6$ .............. A61B 3/14; A61B 3/02; G02C 1/00
[52] U.S. Cl. .............. 351/209; 351/243.1; 351/237; 351/158
[58] Field of Search ............... 351/209, 222, 351/237, 243, 206, 246, 158

[56] References Cited

U.S. PATENT DOCUMENTS

| | | | |
|---|---|---|---|
| 4,852,988 | 8/1989 | Adachi | 351/210 |
| 5,325,133 | 6/1994 | Adachi | 351/209 |

FOREIGN PATENT DOCUMENTS

| | | |
|---|---|---|
| 0 547 931 A1 | 6/1993 | European Pat. Off. . |
| 0 588 290 | 3/1994 | European Pat. Off. . |
| 2684285 | 6/1993 | France .............. 351/209 |
| 2 276 467 | 9/1994 | United Kingdom . |
| WO 92/21999 | 12/1992 | WIPO . |

OTHER PUBLICATIONS

Charbonnier, et al., "Gas-Controlled Display," *ORIA* -pp. 291-296 (1994).

*Primary Examiner*—Huy Mai
*Attorney, Agent, or Firm*—Burns, Doane, Swecker & Mathis LLP

[57] ABSTRACT

The invention concerns a device for measuring the position of the fixing point (P') of an eye on a video screen (19) comprising: a mobile support (10) positioned close to the eye and on which first illumination means (12) and a video camera (11) are fixed so as to embody images of the eye, and a fixed support (17) distant from the eye and on which the video screen orientated opposite the eye and a plurality of luminous sources illuminating the eye in alternative with the first illumination means are positioned and disposed around the video screen so as to create on the eye corneal reflections and means (20) for treating the images obtained from the eye. The invention also concerns an eye illumination method in which the eye is illuminated by flashes each emitted at the end of each taking of images, as well as an application of the device for displaying on the video screen images which change according to the movements of the eye wherein a high resolution zone (Z) is defined around the fixing point (P') and for moving this zone according to the movements of the eye. Application for the medical sphere, ergonomics and interactive data processing.

8 Claims, 5 Drawing Sheets

DEVICE FOR MEASURING THE POSITION OF THE FIXING POINT OF AN EYE ON A TARGET, METHOD FOR ILLUMINATING THE EYE AND APPLICATION FOR DISPLAYING IMAGES WHICH CHANGE ACCORDING TO THE MOVEMENTS OF THE EYE

FIELD OF THE INVENTION

The invention concerns a device for measuring the positioning of the fixing point of an eye on a target, such as a video screen. It also concerns a method for illuminating the eye implemented by this device, as well as an application for displaying images according to the gaze of the subject and more particularly for displaying a zone of interest around the fixing point of the eye and for moving this zone of interest according to the gaze of the subject.

The device and method of the invention can be used in interactive computer applications where the data submitted on the screens depends on the position of the gaze. More particularly, the invention is applicable to the field of ergonomics for analyzing the strategy for taking visual information and the fatigue of a subject working on a working station. It can also be used in medical applications for assisting tetraplegic handicapped persons who are able to activate controls by designating functional boxes on a screen.

BACKGROUND OF THE INVENTION

The eye is a human organ and has been extensively studied, especially concerning its movements. FIG. 1 diagrammatically shows a front view of an eye. This eye comprises an eye-socket 1, the eyelid 2 being located above said eye-socket. Inside the orbit 1, it is possible to see a portion of the sclera 3 which forms a sort of white sphere having a circular opening where the cornea 4 is inserted, slightly more bulged than the sclera 3. The cornea 4 is transparent and thus makes it possible to see the iris 5 which is an opaque membrane pierced with a circular opening, namely the pupil 6. This figure also shows a corneal reflection 7, that is the reflection which can be seen on the cornea 4 when the eye is illuminated from the front.

As shall be seen later in the description, several corneal reflections may be visible on the pupil 6, the sclera 3 or on the iris 5 when several light sources illuminate the eye.

Normally, the measuring of the movement of an eye consists of determining the position of the pupil and a corneal reflection of the eye. However, when the eye is lit up without taking particular precautions, the images embodied may contain certain dark portions, such as the eyelashes and the eyebrows which merge with the dark disk of the pupil. Similarly, certain light portions of the embodied image, such as the reflections on the skin of the eyelids 2 or the white of the sclera 3, may be merged with the bright stain of the corneal reflection 7. These dark or light portions respectively distort the calculation of the center, pupil or the corneal reflection respectively.

The patent application FR-A-2 684 285 offers a method and device for improving the quality of the images to be treated and thus the precision of the measurements of the position of the eye determined on the basis of these images. This method consists of illuminating the eye, alternatively or simultaneously, by two light sources of distinct directions.

According to this document, the movements of the eye are measured in a mark linked to the head of the subject. This accordingly results in a slight constraint as regards the subject. In fact, in order to know the position of the gazer on a screen, it is therefore necessary to immobilize the head of the subject in front of the screen.

In addition, this method and device are unable to determine the position of the gaze point on a video screen in real time.

However, there are measuring systems able to determine the position of the fixing point of an eye on a video screen. One of these systems is described in the article entitled <<A study of human interface using an eye-movement detection system>> by M. IIDA, A. TOMONO and Y. KOBAYASHI in ATR Communications Systems Research Laboratories, Sanpeidani, Inuidani, Seika-cho, Souraku-gun, Kyoto 619-02 (Japan). This system has the drawback of requiring a total or partial immobilization of the head of the patient in front of the video screen or indeed requiring the addition of a system for measuring the movements of the head of the subject.

SUMMARY OF THE INVENTION

The object of the invention is to resolve the drawbacks of the methods and devices described above and is able to implement interactive systems in which the information submitted on the screen depends on the position of the gaze on the screen and do not impose any restriction on the head of the subject and require measurements of the movements of the head of the latter. To this end, it concerns a device and an eye illumination method so as to measure the position of the fixing point of the gaze on a video screen and a method to display images according to the movement of the eye.

More specifically, the invention concerns a device for measuring the position of the fixing point of an eye on a target and comprising a mobile support integral with the head of the subject and positioned close to the eye and on which secured are first eye illumination means and video means to embody images of the eye. In addition, this device comprises a fixed support distant from the eye and on which positioned are firstly the target, orientated approximately opposite the eye, and second eye illumination means able to create corneal reflections on the eye.

According to the invention, the target consists of image display means, such as a video screen.

The second eye illumination means preferably comprise a plurality of infrared light sources disposed around the image display means, each light source creating a corneal reflection on the eye.

According to the invention, the first illumination means and the second illumination means light up the eye consecutively and the video means embody an image of the eye on each illumination.

The device further comprises suitable image processing means:

for firstly determining the center of gravity of the pupil of the eye from an image obtained when the eye is illuminated by the first illumination means, and secondly the positioning of each corneal reflection with respect to the center of the pupil from an image obtained when the eye is illuminated by the second illumination means, and for determining the position of the fixing point on the image display means on the basis of the measurement of the position, of the center of the pupil on the eye.

The invention also concerns an eye illumination method intended to reduce the temporal deviation between the position of the eye and the corresponding nature. This method consists of illuminating the eye by flashes each emitted at the end of each taking of an image of the eye.

The invention also concerns an application of the image display device using the above-mentioned illumination method. This application consists of determining on an image displayed on the display means a zone of interest (Z) situated around the fixing point (P') and of moving this zone of interest according to the movements of the eye.

When the eye is blinking, the movement of the observation zone is carried out between the start and end of a particular blinking.

DETAILED DESCRIPTION OF THE PREFERRED EMBODIMENTS

Figure 2:
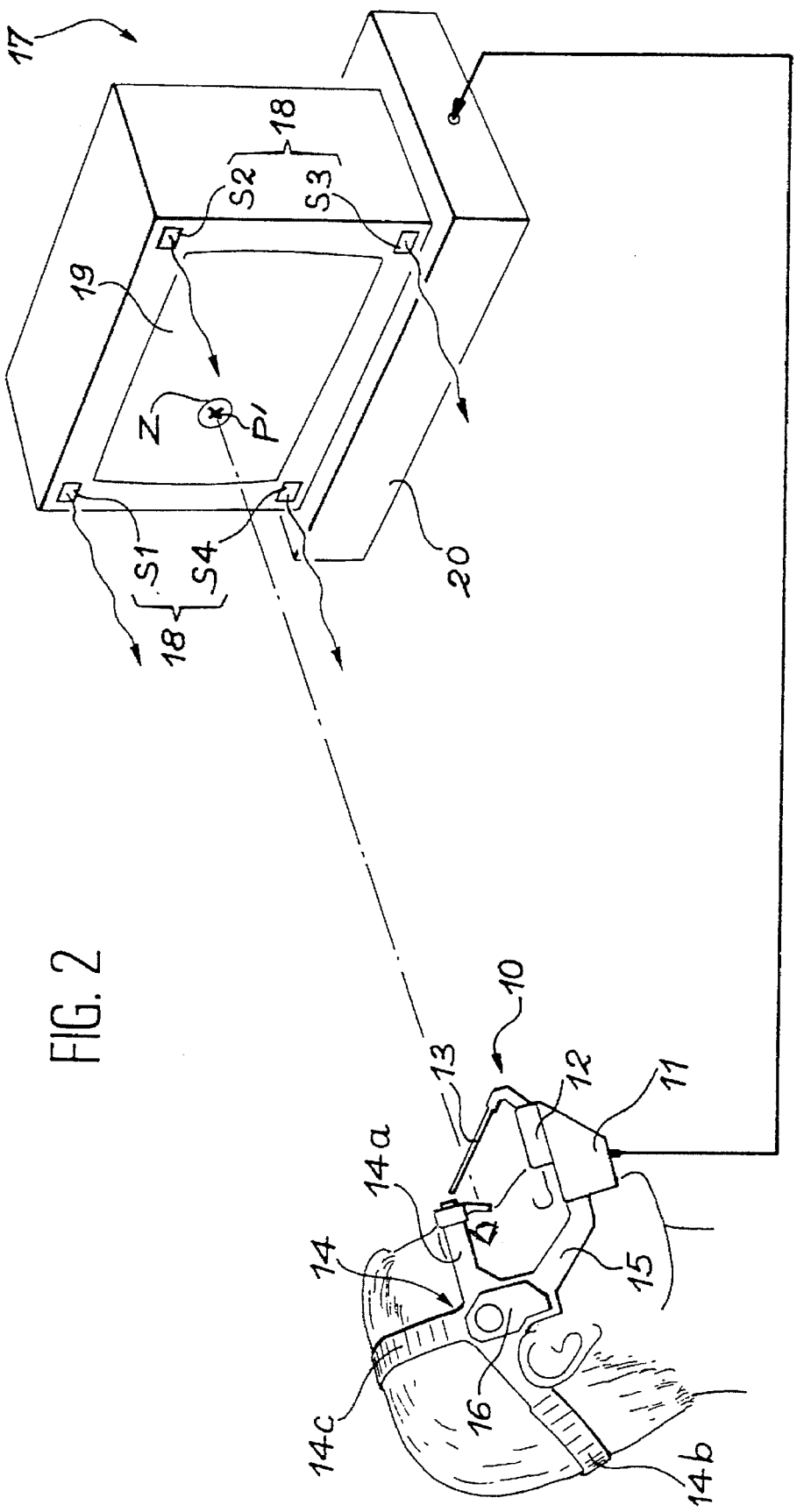
FIG. 2 diagrammatically represents the device for measuring the position of the fixing point conforming to the invention, FIGS. 3A and 3B each diagrammatically represent an eye example on which appear are the corneal reflections and the position of the center of gravity of the pupil.

FIG. 2 diagrammatically shows the device of the invention for measuring the position of the eye fixing point on the video screen.

This device includes a mobile measuring unit 10 or mobile support able to be disposed close to the eye. This mobile support 10 comprises image taking means, such as a miniature CCD video camera 11 and a light source 12 which emits light rays to the semi-transparent mirror 13 slanted in such a way as to send back the light onto the eye of the subject for whom it is sought to discover the position of his gaze on the target 19.

This mobile support may be installed on a spectacle frame, headphone or any other support able to be adapted to the head of the subject.

According to the embodiment example shown on FIG. 2, the measuring unit 10 is mounted on a spectacle frame 14. The camera 11 is secured to the spectacle frame 14 by means of a camera support 15. Mechanical adjustment means 16 adjust the position of the camera support 15 with respect to the frame 14 so as to render the device adaptable to any subject. These adjustment means 16 are situated on the spectacle frame 14 and more specifically on the branch 14a of the frame, the two branches able to be connected by one of several flexible belt type linking strips 14b making it possible to be freed of most of the residual movements of the spectacle frame 14 with respect to the head of the subject.

The device of the invention further includes a fixed support 17 on which image display means 19 are positioned or a video screen constituting the target looked at by the eye of the subject. Also secured to this fixed support 17 are the second illumination means 18, the first illumination means being the source 12 mounted on the mobile support. These illumination means 18 comprise a plurality of infrared light sources disposed around the video screen 10. On the embodiment shown on FIG. 2, the number of these sources is four and are distributed at each corner of the video screen 19. They are given the references S1, S2, S3 and S4. These sources S1, S2, S3 and S4, when they illuminate the eye, create reflections, respectively R1, R2, R3 and R4 and known as corneal reflections, on the pupil, iris or even the sclera of the eye.

The device of the invention further comprises processing means 20 for determining, on the basis of the images taken of the eye, the position of the fixing point on the target 19, that is on the video screen 19.

The camera 11 is electrically connected to the processing means 20 so that the images of the eye obtained by the camera are sent directly to the processing means 20 so as to be processed. These processing means 20 are able to determine firstly the center of gravity of the pupil, and secondly the position of the corneal reflections with respect to this pupil center. The method for calculating this data shall be described in more detail later in the description.

These processing means are preferably positioned on the fixed support 17. According to one embodiment of the invention, these processing means 20 associated with the video screen constitute a computer.

Shown by a cross on the video screen 19 is the position P' of the fixing point of the eye of the subject on the screen and by a square, the zone of interest Z surrounding this fixing point. This zone of interest is an observation zone which corresponds to a portion of the visual field covered by the fovea of the eye. It corresponds to a zone centered around the point P' where the keenness of sight of the subject is maximum with respect to his keenness of sight for the entire field of vision. Its role shall be described in more detail in the rest of the description.

Figure 3A:
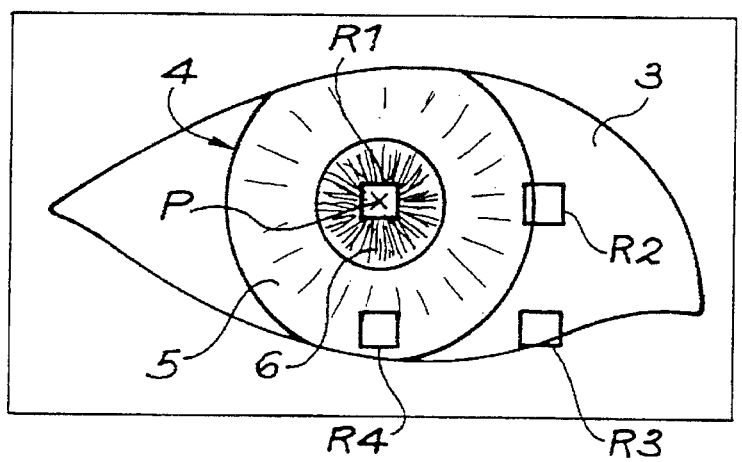
Figure 3B:
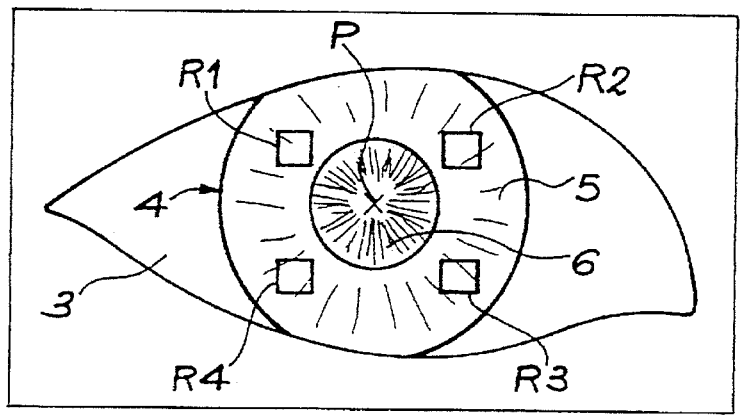

FIGS. 3A and 3B diagrammatically show two examples of corneal reflections on an eye.

As explained earlier, the corneal reflections are the reflections from the light sources S1 to S4 on the cornea 4 or the sclera 3 of the eye. The position of these reflections on the eye depends on the position of the gaze with respect to the video screen and thus with respect to the light sources S1 and S4 which surround the video screen.

FIG. 3A illustrates an example of corneal reflections R1, R2, R3 and R4 on the eye. The point P represents the position of the center of gravity of the pupil 6. This center of gravity P of the pupil 6 is detected and calculated from an image made by the camera when the eye is illuminated by the light source 12 situated on the mobile support. The corneal reflections R1 to R4 are detected from an image made by the camera when the eye is illuminated by the light sources S1 to S4 situated on the fixed support. These two illumination means (firstly, the source 12 and secondly the sources S1 to S4) therefore consecutively illuminate the eye and, on each illumination sequence, an image of the eye is taken. A pair of images of the eye is therefore necessary to determine the position of the reflections R1 and R4 with respect to the center P of the pupil 6.

Figure 1:
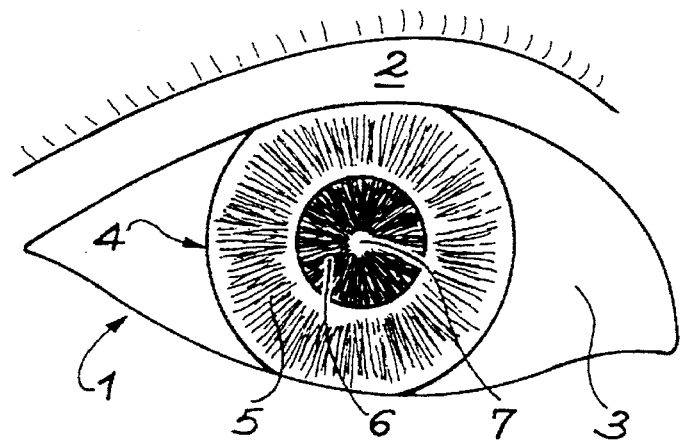
FIG. 1, already described, shows a front view of the eye.

FIG. 1 shows a standard pupil image obtained with the first illumination means. FIGS. 3A and 3B show a standard reflection image obtained with the second means for illuminating an eye.

As regards the example of FIG. 3A, the reflection R1 is merged with the center P of the pupil; the reflections R2 and R3 are positioned mounted on the iris 5 and the sclera 3 of the eye; and the reflection R4 is situated on the iris 5 of the eye. As the center P of the pupil appears on the reflection of the object looked at, in the case of FIG. 3A, it can be deduced that the eye looks at the light source S1 which produces the reflection R1 on the eye.

FIG. 3B illustrates another example of corneal reflections on an eye. According to this example, the center P of the pupil 6 approximately constitutes the center of the polygon formed by the reflections R1 to R4. More specifically, the reflections R1 to R4 are situated on the iris 5 symmetrically in relation to one another with respect to the center P of the pupil. It can be deduced that at the moment images are taken, the subject was in the course of looking at a point close to the center of the video screen.

Figure 4A:
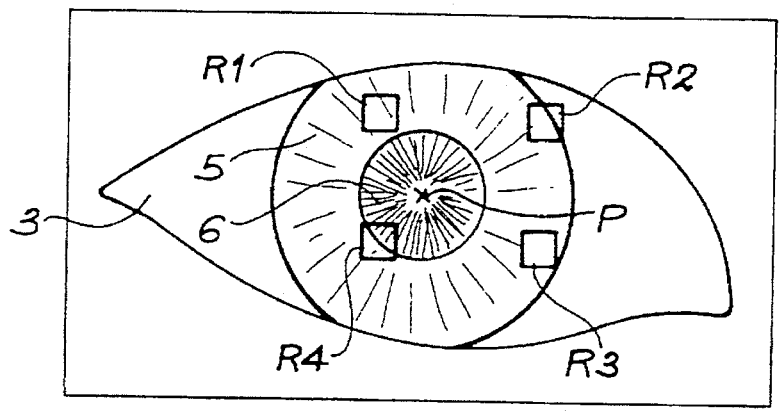
FIG. 4A represents an eye example with corneal reflections and the center of gravity of the pupil.
Figure 4B:
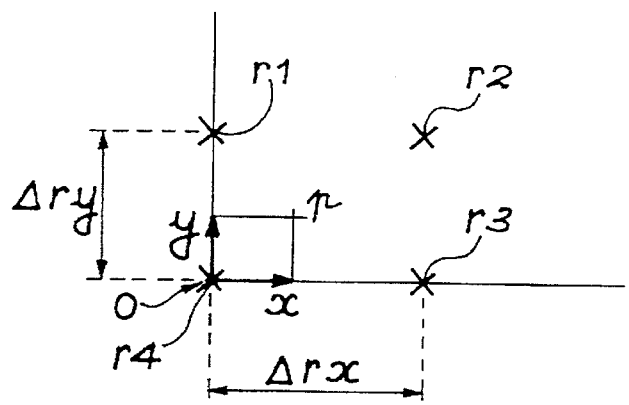
FIG. 4B shows the mark in which the positions are calculated of the corneal reflections shown on the eye of FIG. 4A with respect to the position of the center of gravity of the pupil.
Figure 4C:
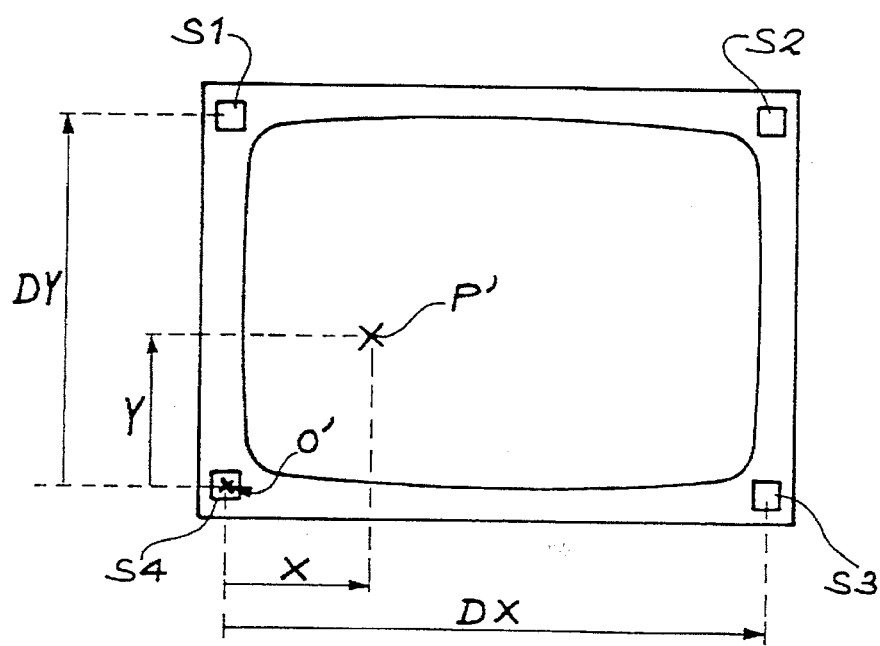
FIG. 4C shows the video screen on which the mark, homothetic to that of FIG. 4B, is noted.

FIGS. 4A, 4B and 4C clearly show how the position of the fixing point P' on the screen is determined from the positions of the corneal reflections R1 to R4 with respect to the center P of the pupil.

FIG. 4A again shows an example of corneal reflections created on an eye by the light sources S1, S2, S3 and S4. In this example, the corneal reflections R1 and R2 are positioned on the iris 5 of the eye; the reflection R3 is situated at the limit of the sclera 3; and the reflection R4 is situated mounted on the iris 5 and the pupil 6.

FIG. 4B shows the mark of the eye from which the positions R1 to R4 are determined with respect to the center P of the pupil. If, as an example, the eye shown on FIG. 4A is considered, the center of grab-gravity of the reflection R4 is r4 which constitutes the origin O of the mark. The center of gravity r3 of the reflection R3 is on the X-axis of the mark at a distance $\Delta Rx$ from the origin O. The center of gravity r1 of the reflection R1 is on the Y-axis of the mark at a distance dry from the origin O; and the center of gravity r2 of the reflection R2 is situated at a distance $\Delta Rx$ on the X-axis and $\Delta Ry$ on the Y-axis with respect to the origin O.

The center P of the pupil is situated in abscissa at a distance x from the origin and in ordinate at a distance y from the origin O, that is from the center of gravity r4.

The coordinates (x,y) thus constitute the position of the center P of the pupil with respect to the centers of gravity r1, r2, r3 and r4 of the reflections R1, R2, R3 and R4 respectively.

FIG. 4C shows the mark linked to the video screen. The light source S4 constitutes the origin O' of this mark. The distances Dx and Dy are respectively the abscissa and ordinate distances from the sources S3 and S1 with respect to the origin O'. The source S2 is at an abscissa distance Dx and at an ordinate distance Dy from the origin O'.

By considering that the mark linked to the screen (O', X, Y) is a homothetic transformation of the mark linked to the eye (O, x, y), it is possible to determine the position of the fixing point P' of the eye on the screen by means of the following homothetic transformation:

$$E1: \quad \frac{x}{\Delta rx} = \frac{X}{DX}$$

$$E2: \quad \frac{y}{\Delta ry} = \frac{Y}{DY}$$

which results in the coordinates (X, Y) of the fixing point P' on the screen:

$$P': \quad X = \frac{x}{\Delta} \frac{DX}{rx}$$

$$Y = \frac{y}{\Delta} \frac{DY}{ry}$$

Thus, the coordinates (x, y) of the center P of the pupil on the eye corresponding to the closet homothetic transformation to the position of the gaze of a subject on the screen.

In practice, it is often preferable to apply to the expressions E1 and E2 corrective coefficients which take account of the geometrical imperfections of the cornea and distortions of the image of the sources S1 to S4 on the cornea.

For example, this device is able to embody an <<ocular mouse>> to replace the conventional mouse connected to the computer. The subject is then able to select his choices from the menus displayed simply by means of his gaze.

The device for measuring the position of the fixing point P' on a screen as described earlier may also be used in a display system controlled by the direction of the gaze. In this case, it is necessary to carry out measurements in real time.

However, there is a certain temporal difference between the measure obtained and the actual position of the eye. The invention thus offers a method enabling this temporal difference to be reduced.

One of the applications is the display on a screen on an image with a non-uniform resolution.

So as to display this image, the method of the invention takes account of a characteristic of the visual system of a human being. In fact, the eye does not take in its entire field of vision with the same keenness: only one zone centered around the fixing point of the eye is seen with clearer definition, the rest of the field of vision being seen with reduced definition. The method therefore consists of using this natural characteristic of the eye by defining around the fixing point on the screen a <<zone of interest>>. This observation zone is also named a high resolution zone in contrast with the remaining part of the image which has a low resolution. This observation zone is represented on FIG. 2 by the circle Z surrounding the point P' for fixing the eye on the screen.

The method then consists of automatically controlling this interest zone around the fixing point, irrespective of the movements of the eye. In other words, the aim of the method of the invention is to ensure the movement in quasi-real time of the observation zone Z defined around the fixing point P' according to the movements of the eye.

This method is implemented by the previously described measuring device since it uses the position measurement determined by this device.

The method of the invention also takes account of a second characteristic of the human eye. In fact, when inspecting the visual field, vision is interrupted several times a second by blinkings, that is the rapid movements of the eye from one fixing point to another. The period of these movements may vary from 20 to 60 ms depending on their amplitude.

In the case of an image presentation system evolving like the subject but according to his gazer it is necessary to display the images, that is move the observation zone sufficiently quickly so that the subject does not notice that only one zone of the image has high resolution, the rest of the image having low resolution.

So as to allow for these visual stimulation modifications, the invention therefore is able to carry out the change of the displayed image, that is move the observation zone during one sudden jerk or immediately at the end of this jerk.

Figure 5:
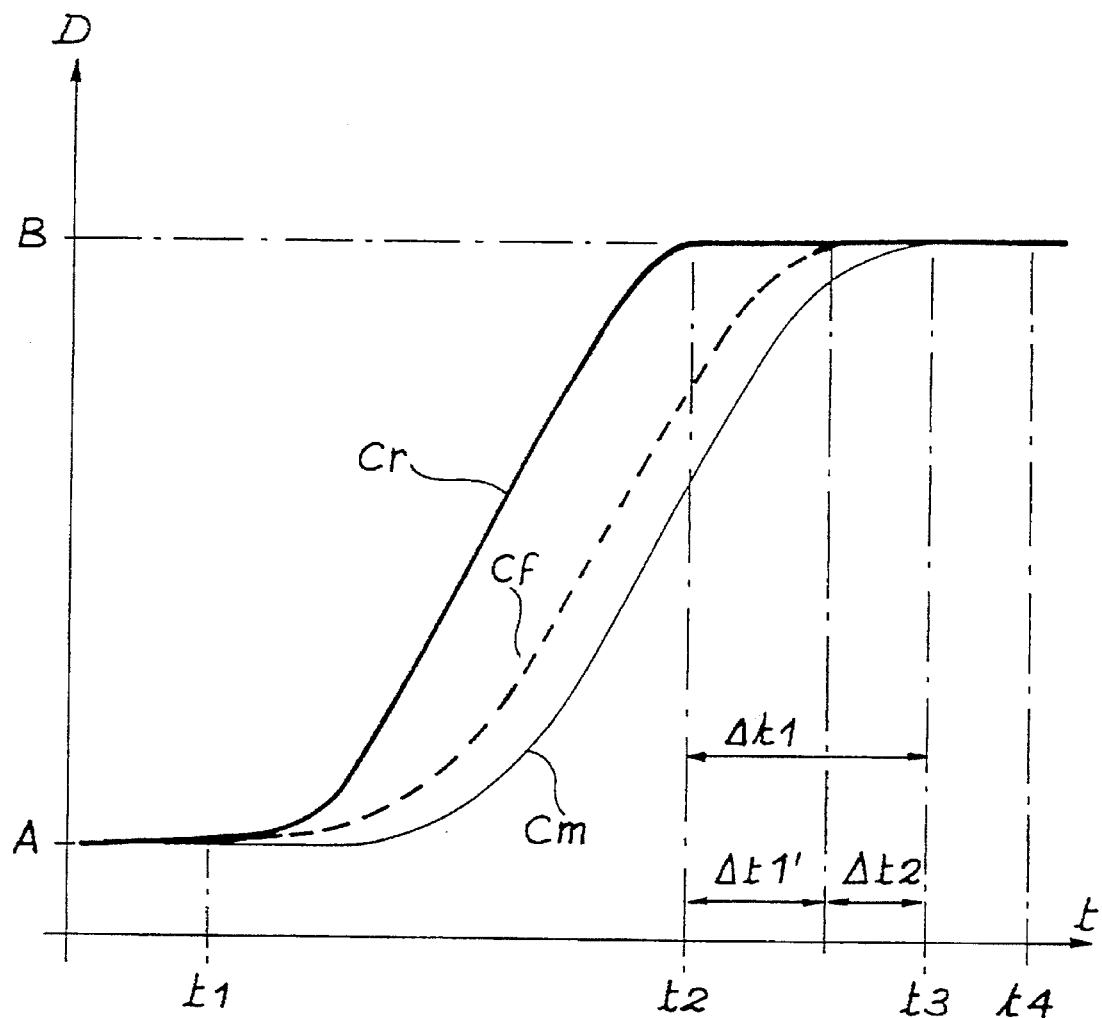
FIG. 5 shows the temporal curves representative of a blinking of the actual eye and the measured eye blinkings.

FIG. 5 shows a curve of the times for a real jerk (Cr) and a curve of the times for a measured jerk (Cm). The curve Cr of FIG. 5 shows the movement on the axis D of the eye according to the time t. According to the example shown by this curve Cr, the eye moves so as to pass from the fixing point A to the fixing point B between the moments t1 and t2, t1 corresponding to the start of the jerk and t2 to the end of the jerk. So as to modify visual stimulation at the fixing point B without the subject noticing, it is necessary to carry out a change of display between the moments t1 and t4, t4 being a moment situated closely after t2, that is shortly after the arrival of the eye at the position B. At this moment t4, the eye has arrived at its new fixing point B from t4–t2. This temporal difference between the jerk end t2 and the moment t3 is called Δt0: this difference may vary according to the individual and nature of the visual stimulation; on average, it equals about 10 ms.

As regards the method of the invention, modification of visual stimulation is selected to be carried out when the eye has reached its fixing point B, that is between the moments t2 and t4. The time needed for cooling of the screen and the calculation of the image adds to the delay Δt1 due to the measuring system of the fixing point P', a delay Δt2. The change of display thus occurs Δt1+Δt2 after the end of the actual jerk.

The curve Cm represents the temporal curve of the measured jerk. The moment t3 of the end of the measured jerk is offset by Δt1 with respect to the end of the actual jerk.

So as to reduce Δt1, the invention illuminates the eye by a flash. This illumination by a flash is also advantageous in that, when the eye blinks, it moves during the image taking time, that is during the period of camera frame. To make this clearly understood, in order to furnish an image, a CCD type video camera integrates the light received for the period of one frame, namely about 16 ms for a camera furnishing 60 images/second.

If during the period of one frame, a jerk occurs during which the eye moves, the image obtained is then out of focus and the measurement of the direction of the gaze is erroneous. The method of the invention therefore is able to embody instantaneous images of the eye by illuminating this eye by luminous flashes. These flashes may be emitted at any time when taken the image. This image taking corresponds to the integration of the light by the CCD detectors of the camera for the period of a frame including a flash.

Figure 6:
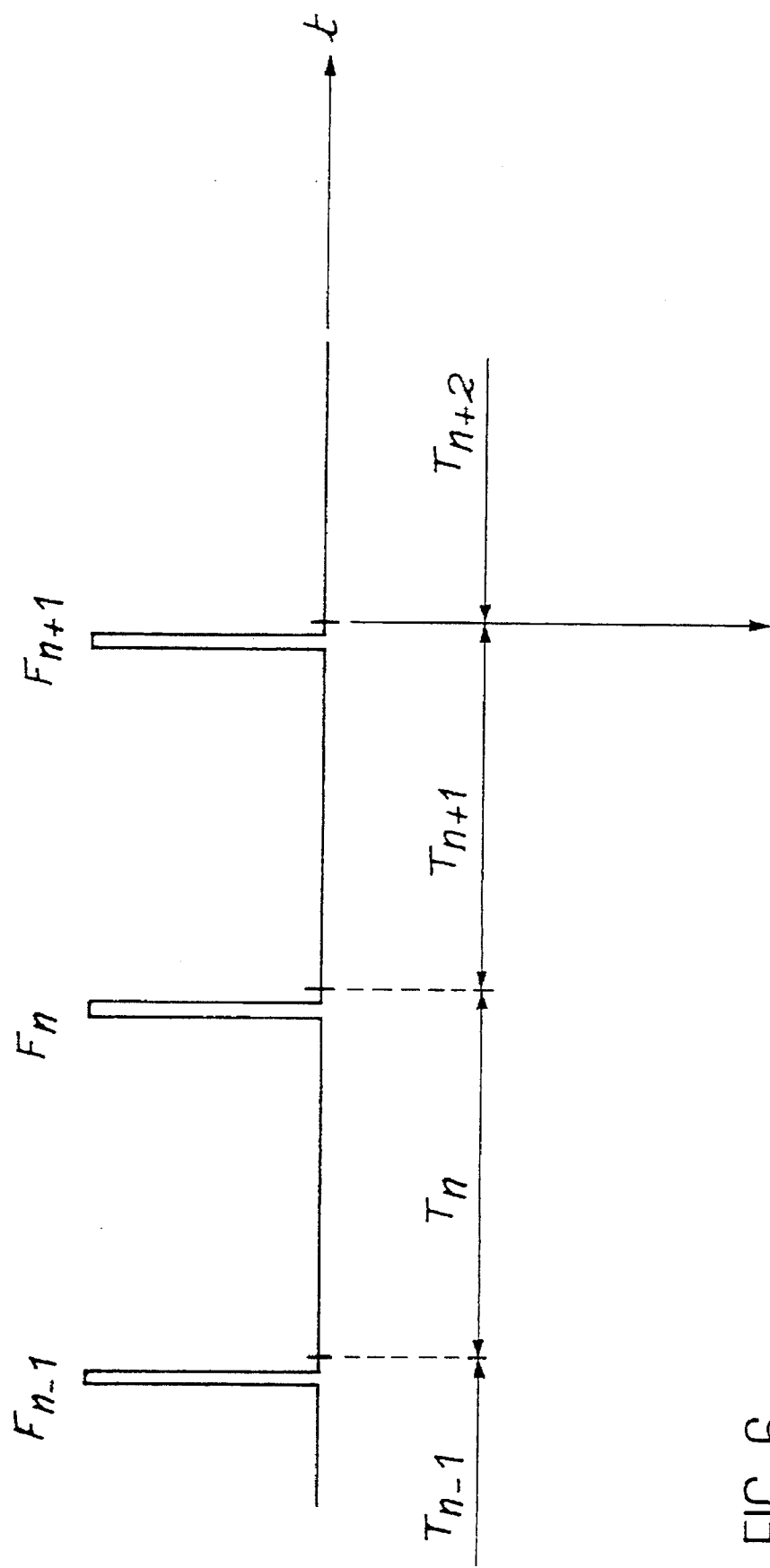
FIG. 6 represents a temporal diagram explaining the illumination of the eye during the taking of images.

Moreover, by illuminating the eye by a flash at the end of each frame, it is possible to limit the temporal difference between the measurement of the position of the eye at the moment of the flash and the moment of the flash itself to the period of one frame. FIG. 6 shows a temporal diagram indicating the temporal position of the flashes Fn−1, Fn and Fn+1 during the frames Tn−1 to Tn+2. This figure shows that each flash Fn−1, Fn and Fn+1 occur immediately before the end of its corresponding frame, respectively Tn−1, Tn and Tn+1. The moment of each frame end Tn−1, Tn and Tn+1 is indicated on the axis of the times t by END Tn−1, END Tn and END Tn+1.

In the example of the taking of an image of the eye during the frame Tn, at the end of a first frame Tn, the flash Fn is triggered so as to illuminate the eye; the reading of the CCD detectors by the electronics of the CCD camera is made during the next frame Tn+1. At the end of the next frame Tn+1, after reading of the CCD detectors of the camera at the measurement of the position of the eye at the moment of the flash Fn is determined and simultaneously the eye is illuminated by the next flash Fn+1 immediately before the end of the frame Tn+1 (the moment when this measurement is carried out is also shown on FIG. 6 for better understanding of the illumination method).

This FIG. 6 thus makes it possible to understand how the eye illumination method of the invention is able to reduce the delay between the moment of obtaining the measurement of the position of the eye and the illumination moment.

The curve Cf on FIG. 5 represents the temporal curve of the jerk measured when there is illumination by flash. It shows that by illuminating the eye as explained earlier, the jerk measured Cf is only offset by one interval Δt1' (with Δt1'<Δt1) of the real jerk Cr. This flash illumination thus has the double advantage of ensuring a clear image of the eye and of reducing the delay between the taking of an image and the result of the measurement so as to allow for a quasi-real time displaying of images.

We claim:

1. Device for measuring the position of the first mobile support (10) integral with the head of the subject and positioned close to the eye and on which secured are first means (12) for illuminating the eye and video means (11) to embody images of the eye, and a support means having a fixed support (17) distant from the eye and on which positioned are firstly the target (19) orientated so as to be approximately opposite the eye, and secondly second eye illumination means (18) able to create on the eye corneal reflections (R1, R2, R3, R4).

2. Measuring device according to claim 1, wherein the target consists of image display means.

3. Measuring device according to claim 2, wherein the second eye illumination means comprise a plurality of infrared light sources (S1? S2, S3, S4) disposed around the image display means, each light source creating a corneal reflection on the eye.

4. Measuring device according to claim 1, wherein the first illumination means and the second illumination means illuminate the eye consecutively and the video means embody an image of the eye for each of the illuminations.

5. Measuring device according to claim 4, further comprising an image processing means (20) for determining the center of gravity of the pupil of the eye from an image obtained when the eye is illuminated by the first illumination means, as well as the positioning of each corneal reflection with respect to the center of the pupil from an image obtained when the eye is illuminated by the second illumination means, and secondly for determining the position of the fixing point (P') on the image display means on the basis of the measurement of the position of the center of the pupil on the eye.

6. A method for taking images of the eye comprising the steps of:

measuring the position of the first mobile support (10) integral with the head of the subject and positioned close to the eye and on which secured are first means (12) for illuminating the eye and video means (11) to embody images of the eye, and a support means having a fixed support (17) distant from the eye and on which positioned are firstly the target (19) orientated so as to be approximately opposite the eye, and secondly second eye illumination means (18) able to create on the eye corneal reflections (R1, R2, R3, R4);

taking images of the eye with the video means; and illuminating the eye by flashes, each emitted at the end of each taking of images of the eye.

7. A method according to claim 6, further including the steps of determining on an image displayed on the display means a zone of interest (Z) situated around the fixing point (P') and moving this zone of interest according to the movements of the eye.

8. A method according to claim 7, wherein, when the eye is blinking, the movement of the zone of interest is carried out during a short period of time (t2, t4) after the end of blinking.

\* \* \* \* \*